US00PP20792P3

(12) United States Plant Patent
Deng et al.

(10) Patent No.: US PP20,792 P3
(45) Date of Patent: Feb. 23, 2010

(54) ***CALADIUM* PLANT NAMED 'CRANBERRY STAR'**

(50) Latin Name: *Caladium×hortulanum*
Varietal Denomination: Cranberry Star

(75) Inventors: Zhanao Deng, Wimauma, FL (US); Brent Harbaugh, Wimauma, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/151,984

(22) Filed: Jun. 26, 2008

(65) Prior Publication Data

US 2009/0328261 P1 Dec. 31, 2009

(51) Int. Cl.
*A01H 5/00* (2006.01)

(52) U.S. Cl. ..... Plt./373

(58) Field of Classification Search ..... Plt./373
See application file for complete search history.

*Primary Examiner*—Annette H Para

(57) ABSTRACT

A new and distinct cultivar of *caladium* named 'Cranberry Star', characterized by its heart-shaped leaves, bright white color and numerous purple spots, and demonstrated potential to produce attractive plants when forced in containers without de-eyeing and/or when grown in outdoor shady landscapes.

1 Drawing Sheet

BACKGROUND OF THE INVENTION

'Cranberry Star' originated from a controlled pollination between the lance-leaved *caladium* (*Caladium×hortulanum*) C35a and the *caladium* UF-85245 in a greenhouse in Bradenton, Fla., and was initially evaluated in 2001 as UF-75-37. Its seed parent, C35a, was derived from the unpatented commercial cultivar Gingerland, and its pollen parent, UF-85245, was from a cross between two unpatented commercial cultivars, 'Aaron' and 'Candidum Junior'. The ancestry of 'Gingerland' and 'Aaron' is unknown, but 'Candidum Junior' is believed to be a field mutation of 'Candidum' (Wilfret, 1993). Plant C35a was selected as the female parent because of its bright leaf spots, and UF-85245 was selected because of its numerous leaves, bright white leaf color, and high tuber yield. Asexual propagation by tuber division has been done in Wimauma, Fla. Evaluation in field and pot studies since 2001 have shown that the unique features of 'Cranberry Star' are stable and reproduced true to type in successive generations of asexual propagation.

SUMMARY OF THE INVENTION

*Caladiums* [*Caladium×hortulanum* Birdsey, Araceae Juss.] are tropical ornamental aroids often used as potted plants or for providing color in the landscape. They are valued for their bright colorful leaves and commercially propagated through tuber division. Leaf color and coloration pattern in *caladium* is diverse and intriguing, from white, red, and pink, to various shades between them, and from solid, to irregularly spotted, and/or blotched. Major breeding objectives in *caladium* often include development of plants expressing new or novel colors or coloration patterns and improvement of plant performance, leaf development, tuber yield, branching habit, sprouting, etc. These traits are important to production of pot plants and utilization of *caladium* in the landscape. When forced in containers as a potted plant, *caladium* with many leaves that emerge quickly from tubers without de-eyeing are highly desirable. For plants to perform well in the landscape, *caladium* must be brightly colored and develop numerous leaves resulting in good color display.

The new *caladium* plant, 'Cranberry Star', has a unique combination of leaf and tuber characteristics that make it ideal for use as a potted plant or for growing as an accent or border plant in shady landscapes. It produces bright white leaves with green main and secondary veins that are similar to leaves of one of the most popular cultivars 'Candidum', yet it expresses numerous bright purple spots on its leaves like 'Miss Muffet' or 'Marie Moir'. Tubers of this cultivar are multiple-branched, produce multiple leaves, and do not require de-eyeing even when forcing in small containers (11.4 cm in diameter). This trait can save growers' time and costs in preparing tubers for pot forcing (Evans et al., 1992; Harbaugh and Tjia, 1985). In addition, 'Cranberry Star' has significantly higher tuber yields and production value when compared to commercial cultivars that were in tests for two years. All these characteristics should benefit growers producing tubers, those marketing potted or bedding plants, and consumers and landscapers utilizing 'Cranberry Star'.

BRIEF DESCRIPTION OF THE PHOTOGRAPHS

The new *Caladium* has not been observed under all possible environmental conditions. The phenotype may vary somewhat with variations in the environment such as light intensity and temperature, without, however, any variance in genotype.

The accompanying colored photograph illustrates the overall appearance of the new cultivar, showing the colors as true as it is reasonably possible to obtain in colored reproductions of this type. Colors in the photograph may differ slightly from the color values cited in the detailed botanical description, which accurately describe the colors of the new *Caladium.*

The photograph, labeled FIG. 1, illustrates the overall appearance of the new cultivar, 'Cranberry Star'. The photograph is a side perspective view of a typical plant of 'Cranberry Star' grown in a container.

DETAILED BOTANICAL DESCRIPTION

The following is a detailed description of the new variety with color terminology in accordance with British Color Council and The Royal Horticultural Society, Horticultural Colour Chart, except where general color terms of ordinary dictionary significance are obvious. Wherein dimensions, sizes, and other characteristics are given, it is to be understood that such characteristics are approximations of averages set forth as accurately as practicable. The description herein is from 8 week old plants of the claimed variety grown in Wimauma, Fla., in 2005–2006. Plants used for describing color were grown in 11.4-cm containers in a 50% shaded greenhouse from #1 (3.8 to 6.4 cm in diameter) de-eyed tubers.

Botanical classification: *Caladium×hortulanum* cultivar Cranberry Star.

Propagation:

*Type.*—By tuber division.

*Time to develop roots and sprout.*—32 days (Spring — 15° C. night to 29° C. day). 18 days (Summer — 21° C. night to 35° C. day).

*Root description.*—Dense, moderately thick roots (up to 2.5 mm at the basal end) with little branching and few lateral roots.

Plant description:

*Plant shape.*—Upright, symmetrical.

*Plant height.*—About 45 cm from top of soil to top of leaf plane 4 months from planting tubers in ground beds in full sun.

*Leaf blade.*—Leaves are peltate, sagitate-cordate, with palmate-pinnate venation 21–29 cm long and 13–16 cm wide. The center veins are green (RHS 137A). The upper surface has a dark green (RHS 137A) irregular margin, 1–2 mm wide, bordering the entire leaf except for the basal leaf sinus where it is greyed-purple (RHS 185A). Interveinal areas are white (RHS 157C). Leaves have numerous (30 to 160) irregularly shaped (1 to 40 mm in length) greyed-purple (RHS 185A) spots. A very light and inconspicuous netted green (RHS 138C) venation occurs on 75–100% of the leaf surface. The undersurface has a narrow (1–3 mm wide) greyed-green (RHS 191B) margin. Primary veins are greyed-green (RHS 191B), and netted venation is greyed-green (RHS 191B) and occurs over the entire leaf surface. Interveinal areas are quite variable in color with a green-white (RHS 157C) color near the center to a greyed-green (RHS 194D) near the margin. Greyed-purple spots (RHS 186A) are numerous and scattered between primary veins.

*Petiole.*—Petioles are 3–5 mm and are light green at the apex, but the color gradually diffuse into darken brown (RHS 200B) at the petiole base that is around 6 mm in diameter.

*Tuber.*—Tubers are multi-segmented; a tuber 6.4–8.9 cm in diameter will typically bear 5–6 dominant buds. Tuber surfaces are brown (RHS 200C) with the cortical area very yellow-orange (RHS 15C).

*Inflorescence.*—The flowering and reproductive organs do not differ in character from other *caladium* plants.

Performance: 'Cranberry Star' was evaluated for tuber production and plant performance at the Gulf Coast Research and Education Center in Wimauma, Fla. in 2005 and 2006. The soil was an EauGallie fine sand with about 1% organic matter and a pH of 6.2. Plants were grown in a plastic-mulched raised-bed system maintaining a constant water table with seep irrigation. In 2005, ground beds were fumigated on February 25 (6 weeks before planting), with a mixture of 67% methyl bromide and 33% chloropicrin (by volume) at the rate of 392 $kg \cdot ha^{-1}$, and in 2006, the beds were fumigated on March 10, 10 days before planting, with the same fumigant mixture but at 196 $kg \cdot ha^{-1}$. The beds were 91 cm wide and 20 cm high with 2.5-cm *caladium* seed pieces planted 15 cm apart in 3 rows also spaced 15 cm apart. Osmocote 18N-2.6P-10K 8–9 month controlled release fertilizer was applied to the bed surface when shoot tips were emerging from the soil with N at 336 $kg \cdot ha^{-1}$.

Field plots were organized in a randomized complete block design consisting of three replications. For tuber production, each plot was 1.2 $m^2$ and contained 30 propagules. Tubers were graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 cm). The production index is an indicator of economic value of the harvested tubers and was calculated as: N (No.2s)+2N (No. 1s)+4N (Jumbos)+6N (Mammoth)+8N (Super Mammoth); where N=number of tubers in each grade. An analysis of variance was conducted in order to compare the performance of 'Cranberry Star' to that of 'Marie Moir', 'Miss Muffet', and 'Candidum'. 'Marie Moir' and 'Miss Muffet' both have spots on leaves, and 'Candidum' is ranked as one of the best cultivars for tuber production and tuber producers consider it very profitable to grow because it yields so well. For plant performance in the landscape, three plants were measured in the center of each plot and plant height, leaf number, and leaf size were measured mid-summer.

The weight of 'Cranberry Star' tubers was 16% to 81% greater than that of 'Morie Moir', 'Miss Muffet', and 'Candidum' in 2005 and 44% to 220% greater than these cultivars in 2006 (Table 3). The production index for 'Cranberry Star' was 42% to 97% greater than that of 'Marie Moir', 'Miss Muffet', and 'Candidum' in 2005 and 41% to 178% greater than these cultivars in 2006 (Table 3). Although the same number (30) of seed pieces was planted per plot, different numbers of tubers were harvested for different cultivars. *Caladiums* often have several sprouts emerge from a single propagule, resulting in more than one tuber being developed per planted seed piece. In addition, large branched tubers may break apart at weak joints resulting in several smaller tubers. Of course, harvesting a greater number of tubers than the number of seed pieces planted is advantageous as it can increase profitability to field growers. 'Cranberry Star' produced 74 and 45 marketable tubers per plot in 2005 and 2006, respectively, that is 61% to 100% more tubers than 'Marie Moir', 'Miss Muffet', and 'Candidum' in 2005 and 15% to 50% more in 2006. The distribution of tubers among grades also is an important factor for marketing. 'Cranberry Star' had a good distribution of tubers with approximately 90% in the No. 1, Jumbo, and Mammoth categories, similar to that of 'Candidum' and 'Miss Muffet'.

Landscape performance of cultivars grown under full-sun conditions was evaluated on the same plots used for evaluating tuber production. Plant height, number of leaves, and foliar characteristics were recorded approximately 3 and 4 months after planting. The overall plant performance of plants was rated on a scale of 1 to 5, with 1 being very poor (few leaves and lack of vigor), and 5 being excellent (full plants, numerous leaves, and bright color display). 'Cranberry Star' had a rating of 4 at the 3-month evaluation, significantly higher than 'Morie Moir', 'Miss Muffet', and 'Candidum', and a rating of 4.6 at the 4-month evaluation, also higher than the three commercial cultivars.

The suitability for container forcing was evaluated by forcing tubers in 11.4-cm containers. No. 1 tubers were planted either intact or de-eyed in a peat/vermiculite mix (VerGro Container Mix A, Verlite, Tampa, Fla.) on Mar. 26, 2007. The study was conducted in a greenhouse with 50% light exclusion during the summer in Wimauma, Fla. Average daily temperatures ranged from 16° C. night to 29° C. day during the experiment. Potted plants were arranged on mental benches in the greenhouse in a randomized complete block design with 10 replications. Plant height, number of leaves, and foliar characteristics were recorded 8 weeks after planting.

'Cranberry Star' sprouted in 31 (intact) or 33 days (de-eyed) after planting, 4–9 days earlier than 'Marie Moir', similar to 'Candidum Junior', and approximately 4 days later than 'Miss Muffet' (Table 3). Intact plants of 'Cranberry Star' were 22.7 cm tall, similar in height to 'Marie Moir' and 'Candidum Junior', but taller than 'Miss Muffet', a known dwarf cultivar. Plant height was 25.2 cm for de-eyed plants. 'Cranberry Star' had 7 to 8 leaves on intact plants 8 wk after planting, but 13 on de-eyed plants. 'Cranberry Star' leaf size was similar to or slightly larger than 'Candidum Junior', but smaller than 'Marie Moir' and larger than 'Miss Muffet'. 'Cranberry Star' produced high quality plants in small pots (11.4 cm in diameter) even without de-eyeing (Table 2). With tubers de-eyed, 'Cranberry Star' produced 60% to 80% more leaves than the three commercial cultivars and yielded pot plants of even higher quality with a plant quality rating greater than the three commercial cultivars.

TABLE 1

Plant performance approximately 4 months from planting 2.54-cm tuber propagules in ground beds in full sun in 2005 and 2006. Values presented arc means of three replications with three plants measured per plot per year.

| Cultivar | Plant ht (cm) | Leaves (no.) | Leaf Length (cm) | Leaf Width (cm) | Overall plant performance rating[z] 3 months | Overall plant performance rating[z] 4 months |
|---|---|---|---|---|---|---|
| Cranberry Star | 45 | 26 | 26 | 16 | 4.0 | 4.6 |
| Candidum | 34 | 12 | 24 | 15 | 1.5 | 3.1 |
| Marie Moir | 42 | 17 | 27 | 19 | 1.6 | 4.1 |
| Miss Muffet | 22 | 14 | 17 | 12 | 1.3 | 4.2 |
| LSD (α = 0.05) | 8.0 | 3.5 | 5.0 | 2.5 | 0.6 | 0.2 |

[z]Overall plant performance was rated 3 months and 4 months after planting on a scale of 1 to 5, with 1 being very poor, 3 fair and acceptable, and 5 being excellent in plant vigor and fullness.

TABLE 2

Plant performance for *caladium* cultivars grown from No. 1 tubers in 11.4-cm containers in a 50% shaded glasshouse, 2007, Wimauma, Fla. Values represent the means of 10 plants produced from intact or de-eyed No. 1 (>3.8 and <6.4 cm in diameter) tubers planted individually per container.

| Cultivar | Days to sprout[z] Intact | Days to sprout[z] De-eye | Plant ht (cm) Intact | Plant ht (cm) De-eye | Leaves (no.) Intact | Leaves (no.) De-eye |
|---|---|---|---|---|---|---|
| Cranberry Star | 31.1 | 33.2 | 22.4 | 25.2 | 7.4 | 13.2 |
| Candidum Junior | 30.9 | 34.3 | 18.9 | 14.7 | 11.3 | 10.3 |
| Marie Moir | 36.3 | 42.1 | 22.0 | 19.6 | 4.6 | 6.8 |
| Miss Muffet | 27.1 | 30.4 | 15.1 | 15.1 | 8.4 | 18.4 |
| LSD (α = 0.05) | 5.1 | 4.8 | 6.0 | 3.7 | 2.5 | 3.0 |

TABLE 2-continued

Plant performance for *caladium* cultivars grown from No. 1 tubers in 11.4-cm containers in a 50% shaded glasshouse, 2007, Wimauma, Fla. Values represent the means of 10 plants produced from intact or de-eyed No. 1 (>3.8 and <6.4 cm in diameter) tubers planted individually per container.

| Cultivar | Leaf length (cm) Intact | Leaf length (cm) De-eye | Leaf width (cm) Intact | Leaf width (cm) De-eye | Quality rating Intact | Quality rating De-eye |
|---|---|---|---|---|---|---|
| Cranberry Star | 23.1 | 21.1 | 15.4 | 12.9 | 4.0 | 4.9 |
| Candidum Junior | 20.4 | 18.3 | 13.2 | 11.2 | 3.5 | 3.5 |
| Marie Moir | 28.1 | 18.6 | 19.7 | 12.1 | 2.0 | 2.3 |
| Miss Muffet | 19.4 | 15.6 | 12.5 | 8.6 | 3.1 | 4.4 |
| LSD (α = 0.05) | 2.8 | 3.0 | 2.5 | 2.0 | 0.9 | 0.4 |

[z]Number of days from planting to the first unfurled leaf.

TABLE 3

Tuber weights, production index, and tuber grade distribution of *caladium* cultivars harvested in 2005 and 2006. Values presented are means of three replications with 30 propagules per 1.2-$m^2$ plot per year.

| Cultivar | Tuber Weight (kg) | Tuber Production index | Tuber Marketable (number) |
|---|---|---|---|
| **Year 2005** | | | |
| Cranberry Star | 5.8 | 226 | 74 |
| Candidum | 2.6 | 103 | 34 |
| Marie Moir | 5.0 | 159 | 46 |
| Miss Muffit | 3.8 | 115 | 37 |
| LSD (α = 0.05) | 1.4 | 22.4 | 15.3 |
| **Year 2006** | | | |
| Cranberry Star | 4.8 | 161 | 45 |
| Candidum | 3.1 | 114 | 35 |
| Marie Moir | 1.5 | 58 | 30 |
| Miss Muffet | 2.7 | 106 | 39 |
| LSD (α = 0.05) | 1.1 | 36.8 | 9.7 |

| Cultivar | Tuber distribution (%) Super mammoth | Mammoth | Jumbo | No. 1 | No. 2 |
|---|---|---|---|---|---|
| **Year 2005** | | | | | |
| Cranberry Star | 3 | 14 | 25 | 48 | 11 |
| Candidum | 0 | 4 | 48 | 43 | 6 |
| Marie Moir | 2 | 17 | 37 | 36 | 9 |
| Miss Muffit | 0 | 10 | 40 | 40 | 10 |
| LSD (α = 0.05) | ns | ns | ns | ns | ns |
| **Year 2006** | | | | | |
| Cranberry Star | 2 | 18 | 40 | 34 | 6 |
| Candidum | 2 | 12 | 39 | 38 | 9 |
| Marie Moir | 2 | 0 | 12 | 44 | 42 |
| Miss Muffet | 0 | 9 | 29 | 41 | 21 |
| LSD (α = 0.05) | ns | ns | 8.8 | ns | ns |

The production index is an indicator of economic value of the crop harvested and is calculated as: N (No. 2s) + 2N (No. 1s) + 4N (Jumbos) + 6N (Mammoth) + SN (Super Mammoth); where N = number of tubers in each grade. Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 cm).
ns: not significant at P ≦ 0.05.

It is claimed:

1. A new and distinct cultivar of *Caladium* plant named 'Cranberry Star', as illustrated and described, characterized by its heart-shaped leaves, bright white color and numerous purple spots, and demonstrated potential to produce attractive plants when forced in containers without de-eyeing and/or when grown in outdoor shady landscapes.

* * * * *

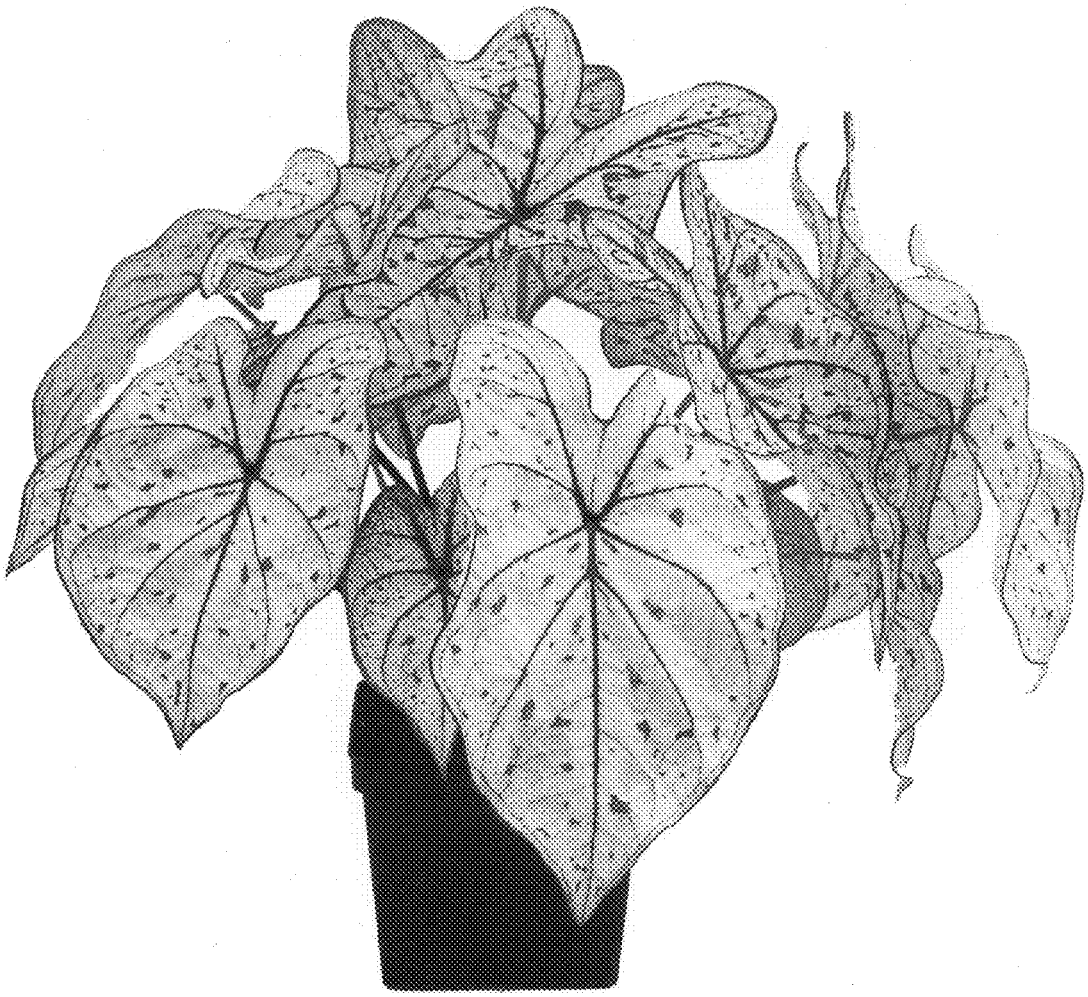
Fig. 1 – Caladium Plant named 'Cranberry Star'